United States Patent [19]

Mazess

[11] Patent Number: 5,481,587
[45] Date of Patent: Jan. 2, 1996

[54] RADIOGRAPHIC PHANTOM FOR VERTEBRAL MORPHOMETRY

[75] Inventor: Richard B. Mazess, Madison, Wis.

[73] Assignee: Lunar Corporation, Madison, Wis.

[21] Appl. No.: 239,664

[22] Filed: May 9, 1994

[51] Int. Cl.[6] .................................................. G01D 18/00
[52] U.S. Cl. ............................................ 378/207; 378/18
[58] Field of Search ........................................ 378/207, 18

[56] References Cited

U.S. PATENT DOCUMENTS

| | | | |
|---|---|---|---|
| 4,126,789 | 11/1978 | Vogl et al. | 250/505 |
| 4,724,110 | 2/1988 | Arnold | 264/102 |
| 5,187,731 | 2/1993 | Shimura | 378/207 |
| 5,235,628 | 8/1993 | Kalender | 378/207 |

OTHER PUBLICATIONS

Hologic QDR–1000, X–Ray Bone Densitometer, Automated QC Protocol Product Information.

Primary Examiner—Craig E. Church
Attorney, Agent, or Firm—Quarles & Brady

[57] ABSTRACT

An x-ray phantom provides at least two vertebral models one of which represents a case of clinically recognized deformity relevant to the evaluation of osteoporosis. The two vertebral models are mounted with respect to each other to simulate a second spine and to permit changing of the attitude and relative orientation of the vertebral models with respect to each other. The mounting may provide variable degrees of spine curvature and permit substitution of different vertebral models simulating different deformities. The vertebral models have known bone mineral densities to permit the evaluation of automatist bone density/morphometry techniques.

18 Claims, 4 Drawing Sheets

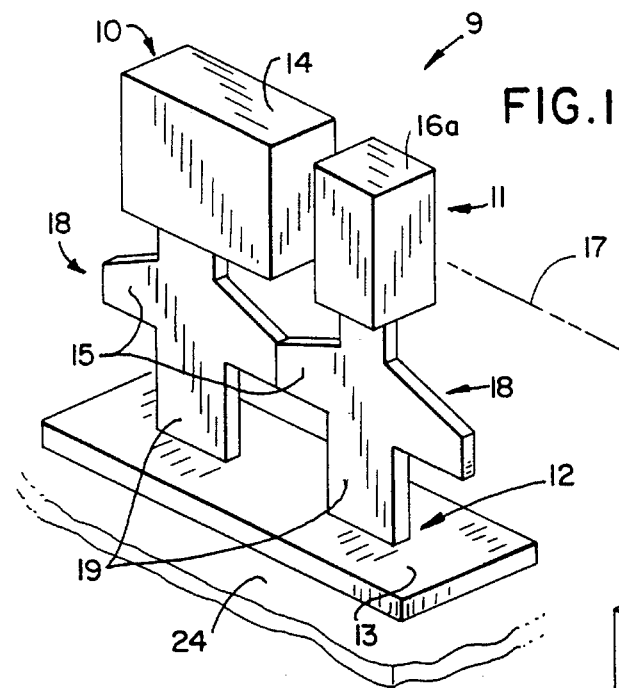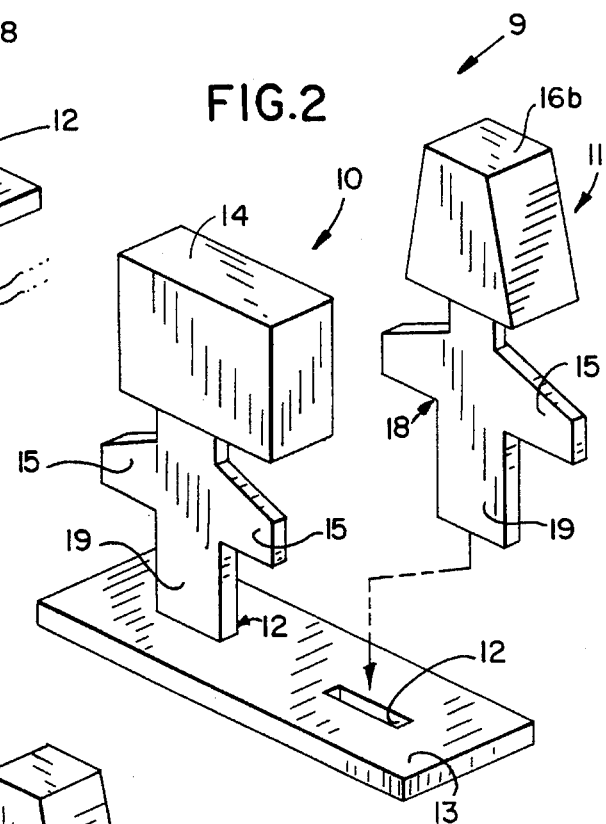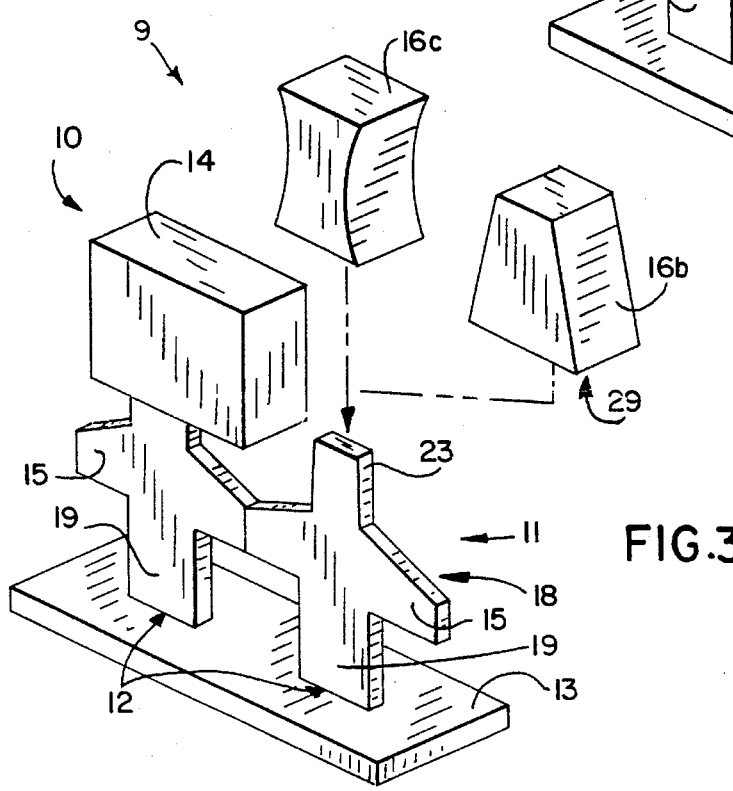

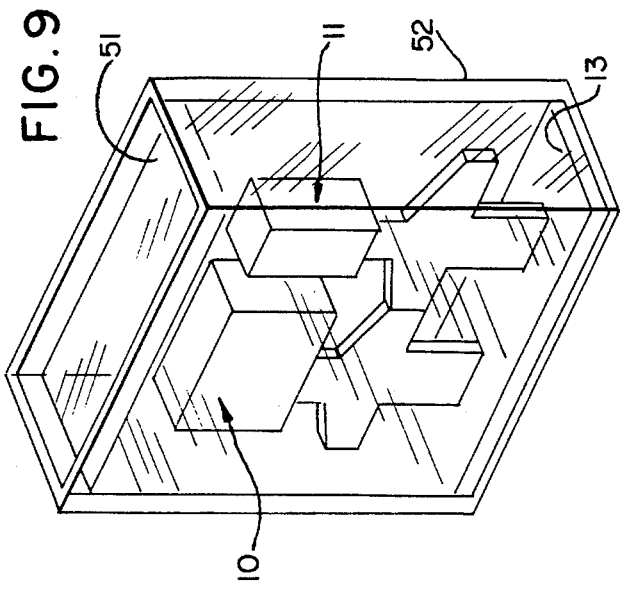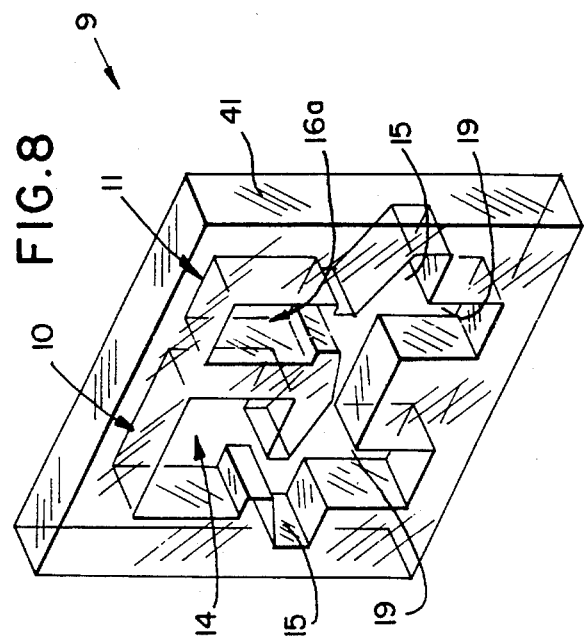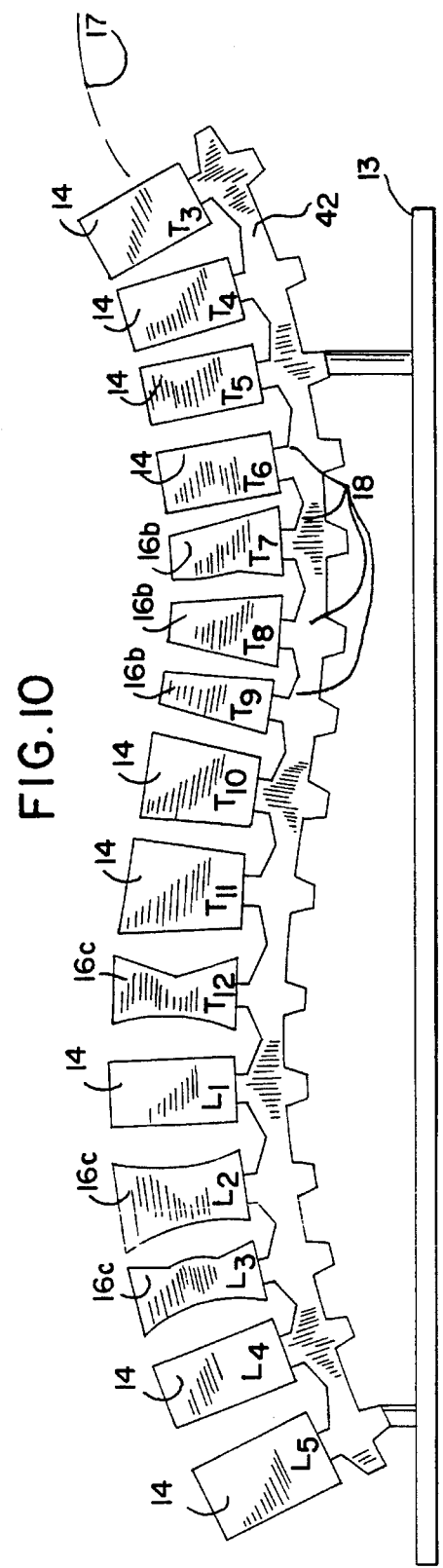

RADIOGRAPHIC PHANTOM FOR VERTEBRAL MORPHOMETRY

FIELD OF THE INVENTION

The present invention relates to a test fixture for radiographic equipment. More particularly, the present invention relates to an x-ray phantom and method of using said phantom for quality assurance and control in studies involving vertebral bone morphometry.

BACKGROUND OF THE INVENTION

The screening and diagnosis of osteoporosis is becoming an increasingly important health care priority. This is because osteoporosis is generally a disease of aging and thus is becoming more widespread with the ever-increasing life span of the world's population. Osteoporosis often results in painful and debilitating fractures of the spine and hip.

Early screening and diagnosis of osteoporosis can result in the afflicted person receiving therapy which may prevent such debilitating fractures. In screening for osteoporosis it is recommended that a physician obtain both a bone density ("BMD") scan of the patient's skeleton, particularly the spine, and lateral x-rays of the spine for evidence of fracture. The combination of low spinal bone density and vertebral fracture is generally accepted as diagnostic of osteoporosis. With today's bone densitometers, the determination of spinal BMD is relatively straightforward. Determining whether there is evidence of vertebral fracture by subjectively evaluating a lateral radiograph tends to be a more problematic task. Hedlund, L. R. and J. C. Gallagher, "Vertebral morphometry in diagnosis of spinal fractures", Bone and Mineral, vol. 5, 59–67 (1988). Even in patients with established osteoporotic fractures it is difficult to reliably indicate the nature and extent of vertebral deformation because there are not consistent criteria for evaluation.

This is because in the early stages of osteoporosis, the subjective examination of a lateral radiograph of the vertebral column is often ineffective in diagnosing vertebral deformation or fracture. This is particularly true if there is no previous radiological record available for comparison. Vertebral deformities or fractures are classified into crush deformities, wedge deformities and end-plate deformities. In the latter type of deformity, one has biconcavity and hypertrophy types of deformities. An early crush fracture often will reveal no sharply defined fracture line and thus it is virtually impossible to subjectively distinguish between a vertebral body with a early crush fracture and a normal vertebral body.

Such diagnosis is more effectively made by conducting what is known as vertebral morphometric analysis. Vertebral morphometric analysis is a detailed examination of the shape and dimensions of vertebral bodies as determined from a lateral radiograph of the spine. Using this method, the clinician obtains an analog x-ray image of the patient's vertebral column using a conventional x-ray machine. The image is printed onto a fixed media such as an x-ray radiographic film print. The print is made to a specific scale relative to the patient's spine, i.e. one-to-one, or a specifically reduced or expanded scale. Then the clinician manually measures the size of the vertebra by using a straight edge ruler and pencil. Using this technique, the clinician actually draws on the film to outline the vertebra, selects the appropriate fiducial points and then measures with the ruler the distance between the fiducial points. The more common measurements made in a vertebral morphometric study are the anterior ($H_a$), middle ($H_m$) and posterior height ($H_p$) of the vertebra. The heights themselves, compared to normal or adjacent vertebra or to a prior study, or the ratio of these heights, one to the other, can be diagnostic of fracture. For example, a decrease in $H_a$ by 15 to 20%, which can be anywhere from 1.8 to 7 mm depending on the size and age of the individual, is considered by some physicians to indicate fracture. See e.g. Smith-Bindman, R. et al., "A Comparison of Morphometric Definitions of Vertebral Fracture", J. Bone and Min. Res., Vol. 6 No. 7, 25–34 (1991).

While the manual technique described above is still widely used, computerized techniques have also become available. One computerized technique requires an analog lateral radiograph which is then digitized. Once digitized, the radiographic image is analyzed using a software program which provides measuring tools but still requires the clinician to manually select the fiducial points for measurement. Nelson, D., et al., Measurement of vertebral Area on Spine X-rays in Osteoporosis: Reliability of Digitizing Techniques, J. Bone and Mineral Research, Vol. 5, No. 7, 707–715, (1990).

More recently, an apparatus and method have been described comprising a digital x-ray machine and software which automatically analyzes the vertebral morphometry. U.S. Pat. No. 5,228,068 issued to Lunar Corporation, incorporated herein by reference, describes such a device. Unlike a conventional x-ray machine which utilizes a cone-shaped x-ray beam, the aforementioned digital x-ray machine utilizes a scanning fan beam. One embodiment of the invention described and claimed in the aforementioned patent is the use of a dual energy x-ray and software which permits not only the analysis of the morphometry of the vertebra but also a determination of bone density of the vertebra.

Regardless of the technique used, distortion of the image can occur leading to erroneous results and misdiagnosis. For example, the conventional x-ray machine, because of the cone shaped x-ray beam, produces a radiographic image which is typically 10–15% larger than life-size, and the magnification is variable depending on the location of the object relative to the plane of the radiograph. Differential magnification occurs due to spine curvature. Distortions of the spine are particularly acute for cone beam exposures at the edges of the cone beam where the ray is most angled. Distortion also occurs because of scattered radiation which causes blurring of the edges thus making it difficult for both the operator and the software to easily detect the edges of the vertebra for measurement.

A scanning fan beam can be used to avoid some of the distortion problems which occur with the conventional cone beam. Blurring because of scattered radiation is greatly reduced in a scanning system. Also, because of the geometry of the beam, magnification in the direction of the scan is greatly reduced. However, distortion can still occur particularly at the edges of the beam where the rays are more angled. Furthermore, as the alignment of the spine is often curvilinear, the desired measurement may not be in the direction of least distortion. Also, the alignment of the fan beam with the detector is more critical with a scanning system than with a conventional x-ray machine and slight misalignment can result in a distortion of the image.

Distortion of the image can lead to misregistration of the software or inconsistent in operator identification of fiducial points. For example, a height measurement may vary if the operator or the computer software is not consistent in selecting the fiducial points. These variations make it difficult to be certain that the measurements are accurate and truly represent the actual morphometry of the patient's vertebrae. Significantly, distortion induced errors in morphometric measurements can not only cause the misdiagnosis of a normal vertebra as having fracture (false positive), but can cause fractured vertebrae to appear normal (false negative).

Both subjective analysis of morphometry by an operator and computer software analysis of a vertebrae may be influenced by a rotation of the vertebra within the image plane and by its relative orientation with respect to its neighbors.

Prior art phantoms exist which purport to allow checking of image magnification and angle settings. One such phantom which is marketed by Cone Instruments and named QA RADIOGRAPHIC PHANTOM has a representative "normal" vertebra. Another phantom is manufactured by Hologic, Inc. of Waltham, Mass. and called the X-CALIBER. However, none of these phantoms permit easy verification that the devices or the software of the newer digital morphometry systems are working properly. None of these phantoms present the types of pathologies that the vertebral morphometry systems are designed to detect and none of these prior art phantoms are suitable for use in the training of techniques required for analyzing vertebral morphometry.

SUMMARY OF THE INVENTION

Since treatment decisions often hinge on finding evidence of vertebral fracture, it is important to know that the image being measured truly reflects the actual size and shape of the vertebra. With the digital, software-assisted systems, there is the additional need to verify that the software is operating properly. There is also a need for a training device which can help train operators in the proper selection of fiducial points and recognition of vertebral deformity. Such a verification system must be able to provide a range of vertebral orientations and shapes to test both for false positives and false negatives in the detection of vertebral fracture.

The present invention is directed to an apparatus that satisfies this need through a relatively inexpensive, easy to use phantom which can be used to calibrate or validate x-ray systems and software used to conduct bone morphometry studies.

Another objective of the present invention is to provide a phantom which can be used in the training of techniques required for analyzing vertebral morphometry.

The phantom of the present invention comprises a material having x-ray absorption and attenuation properties sufficient to allow a negative or positive image to be produced when said material is imaged by an x-ray machine. Said material is formed in a shape sufficient to produce a negative or positive image substantially resembling at least two human vertebrae when the material is imaged by an x-ray machine. At least one of these vertebrae has dimensions consistent with a clinically recognized vertebral deformity such as a crush deformity, a wedge deformity or a biconcavity.

One embodiment of the present invention is a phantom comprised of a material having x-ray absorption and attenuation characteristics similar to bone. The material is formed in the shape of at least two vertebrae, at least one of which resembles a clinically recognized vertebral deformity. The dimensions of each vertebra in the phantom are defined and provide a known measurement for ready validation of the x-ray system and software.

Another embodiment provides interchangeable vertebrae so that the x-ray machine and software can be tested with vertebrae representing different pathologies. The phantom of the invention may also present the vertebrae in a curvilinear arrangement resembling either the natural curvature of the spine or the more pronounced curvature of a diseased spine.

In addition to testing the performance of the x-ray machine and the software with respect to various shapes and sizes, the individual vertebrae may be fabricated so as to have different x-ray attenuation characteristics. Such a phantom could also be used to calibrate bone density measurements.

BRIEF DESCRIPTION OF THE DRAWINGS

These and other features, aspects, and advantages of the present invention will become better understood with regard to the following description, appended claims, and accompanying drawings where:

FIG. 1 shows a perspective view of one embodiment of the invention where one of the vertebra sections represents a normal vertebra and one represents a compressed vertebra;

FIG. 2 shows a perspective view demonstrating the removability of individual vertebra sections where the particular vertebral body being inserted demonstrates a wedge deformity;

FIG. 3 shows a perspective view which shows another embodiment of the invention where the vertebral bodies are interchangeable;

FIG. 8 shows a perspective view of another embodiment of the invention illustrating where the shape of the vertebral bodies are represented in a cut-out;

FIG. 9 shows a perspective view of another embodiment of the invention where the vertebral bodies are encased in a material having attenuation characteristics similar to soft tissue;

FIG. 10 is an elevational front view of another embodiment of the invention where a complete thoracic and lumbar spine are represented.

DETAILED DESCRIPTION OF THE PREFERRED EMBODIMENT

Figure 4:
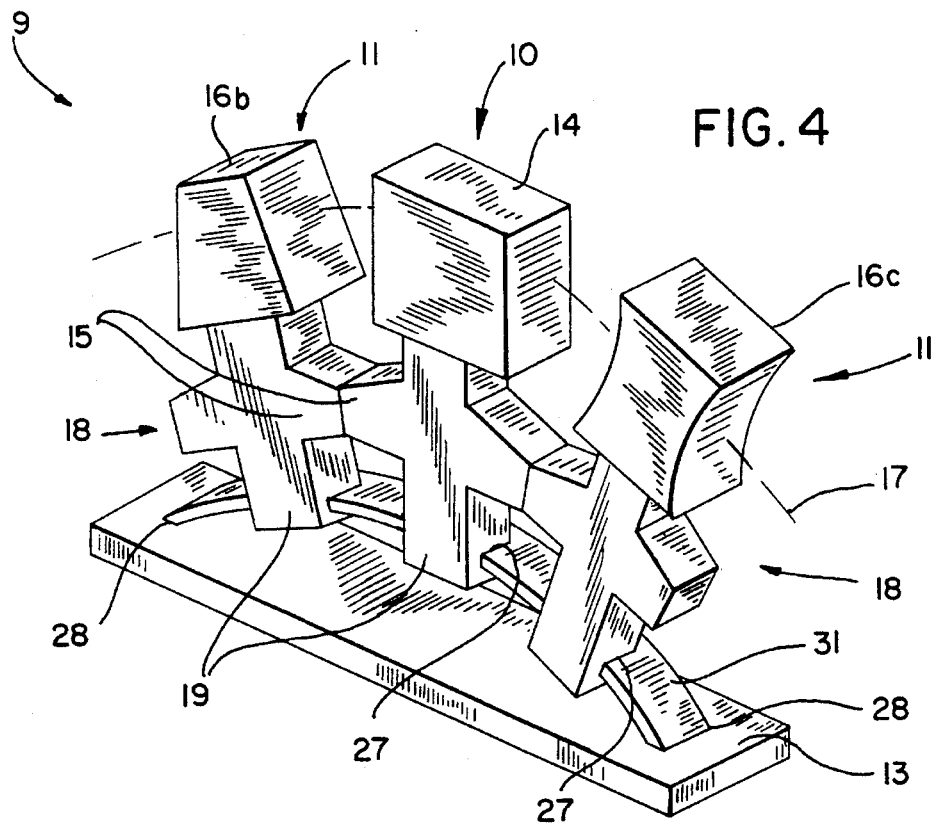
FIG. 4 shows a perspective view of another embodiment of the invention where the vertebra sections are arranged in a curvilinear arc.

The phantom 9 of the present invention, as shown in FIG. 1, includes a generally planar rectangular base 13 sized to be supported against a patient table 24 or the like having a longitudinal axis aligned with the medial axis of a patient when on the table 24 and a transverse axis perpendicular to the medial axis and generally parallel to the surface of the table 24. Formed in the upper face of the base 13, thus displaced slightly above the surface of the table 24, are two rectangular sockets 12 sized each to receive a lower stem 19 of one of two anthropomorphically shaped, representative vertebrae 10 and 11. Each stem 19 has a cross section generally equal to that of the sockets 12 expanding in area as one progresses up the stems 19 to provide a wedging action of the stem 19 in the sockets 12 holding the vertebrae 10 and 11 firmly within the base 13. Other methods of attachment may be used and still would be considered within the scope of the invention. For example, one could provide a pin (not shown) on the base 13 which is inserted into a socket on the stem 19.

The upper end of the stems 19 attach to wing-like posterior elements 18 of the vertebrae 10 and 11 extending longitudinally and simulating the spineous process of the human vertebrae and, in a second embodiment to be described, providing a predetermined minimum separation distance between vertebrae 10 and 11 defined by the abutting of the tips of the wings 15 of the posterior elements 18 when the vertebrae 11 and 18 are not mounted within the base 13.

Atop each of the posterior elements 18 is a vertebral body 14 or 16. One of the vertebral bodies 14, of vertebra 10, resembles a normal, unfractured vertebra, whereas the other vertebral body 16, of vertebra 11 resembles a vertebra having a clinically recognized deformity, in this case. The two vertebra 10 and 11 thus model a portion of the human spine, elevated above but extending generally horizontally, along the length of the base 13.

In the preferred embodiment, the vertebral bodies 14 and 16 are formed of a material having x-ray absorption and attenuation characteristics similar to bone. Suitable materials would be aluminum or epoxy-resin-based plastics or polyethylene plastics containing hydroxyapatite ("HA") in sufficient quantity to give the vertebrae bone equivalent x-ray absorption and attenuation characteristics at multiple x-ray energies. The formation of phantoms from such materials is well known in the art and is described in such publications as U.S. Pat. Nos. 4,126,789, 4,724,110, and 5,235,628, incorporated herein by reference.

In using the phantom of the present invention, the phantom 9 is placed on the patient table 24 of an x-ray machine or densitometer with morphometry capabilities with the spinal axis 17 in the approximate position that the patient's spine would be if the patient were imaged for purposes of vertebral morphometric analysis. If the machine being calibrated is an x-ray machine, an image is made of the phantom 9 and an x-ray film printed. The morphometry analysis is then made using the x-ray film either by making measurements directly on the film or digitizing the film and making the measurements using morphometry software. In either case, the measurements from the film are compared with measurements made directly on the phantom. In automated analyses systems, the accuracy of the detection of deformed vertebrae can be compared to the known dimensions of the vertebral bodies 14 and 16 and hence their implicit status as deformed or normal. For example, one could compare the measurement of $H_m$ of representative vertebral body 14 (the height of the center of the vertebral body 14 or 16 along the axis 17 of the spine) measured directly on the phantom 9 with the same measurement made on the x-ray film image of the phantom 9.

In the case of a densitometer with morphometric capabilities, one can compare both the measured bone density values and the measured morphometric values with direct measurement of the phantom and its known composition. In systems that combine the measurement of morphometry and bone density to attempt to detect osteoporosis, the classification of the vertebral bodies may be evaluated.

Significantly, both normal and deformed vertebra are provided in one phantom 9 so that both false positive and false negative errors may be discerned either in morphometric measurement, bone density measurement and the evaluation of osteoporosis whether by machine or human operator.

Referring now to FIG. 2, the individual vertebra 10 and 11 of the phantom may be removed from the base 13 by removing stems 19 from the sockets 12 and a vertebra 11' representing a different clinically recognizable condition inserted in its place. For example, the deformed vertebra 11' of FIG. 2 may have a vertebral body 16(b) representative of a wedge deformity where the end plates of the vertebral body are not parallel but slope together as one moves away from the base 13. The stem 19 of the posterior elements 18 of the representative deformed vertebra of FIG. 2 is inserted into a socket 12 in the base 13.

In another embodiment illustrated in FIG. 3, the posterior elements 18 are fixed to the base 13 and the representative vertebral bodies, 16(b) and 16(c) are inserted onto a wedge shaped pedicle 23 atop the posterior element 18. The pedicles 23 fit into correspondingly sized rectangular slots 29 (not visible) on the bottom surfaces of the vertebral bodies 16(b) and 16(c) to provide a wedging fit eliminating movement. Here, vertebral bodies 16(b) and 16(c) represent biconcavity (concave endplates) and a wedge deformity, respectively. In this embodiment, the posterior elements 18 may be formed as one unit joined at the wings 15. As with the embodiment in FIG. 2, the means of attachment of the vertebral body to the pedicle can vary and still be considered to fall within the scope of the claims.

As noted above, it is believed that the orientation of the vertebral bodies 14 and 16 with respect to the acquisition of the image (and hence with respect to the base 13) and with respect to each other, affect morphometric measurements either as a result of internal operation of measuring software or because of subjective effects on a human observer caused by the tipping and the change in proximity with other vertebral bodies. Accordingly, as shown in FIG. 4, the vertebral bodies 14 and 16 are presented in a curvilinear arrangement. Here, the representative vertebrae 16(b), 14, and 16(c), are fitted onto a flat metal spring 31 which forms a mounting rail may be curved to produce a curved spinal axis 17.

The vertebrae 10 and 11 are held to the metal spring 31 by longitudinal slots 27 cut generally parallel to the spinal axis 17 in one vertical face at the lower end of the stems 19. These slots 27 are sized to easily receive the metal spring 31 when the latter is straight. Curvature of the metal spring 31 provides a camming action between the spring and the walls of the slot, locking the vertebra 10 or 11 in place. Spacing of the vertebra along the spring 31 is provided by the wings 15 of the posterior elements 18 of the vertebra 10 and 11. The flat metal spring 31 extends along the length of the base 13 with its ends fitting into respective sockets 28 in the base 13.

Figure 5:
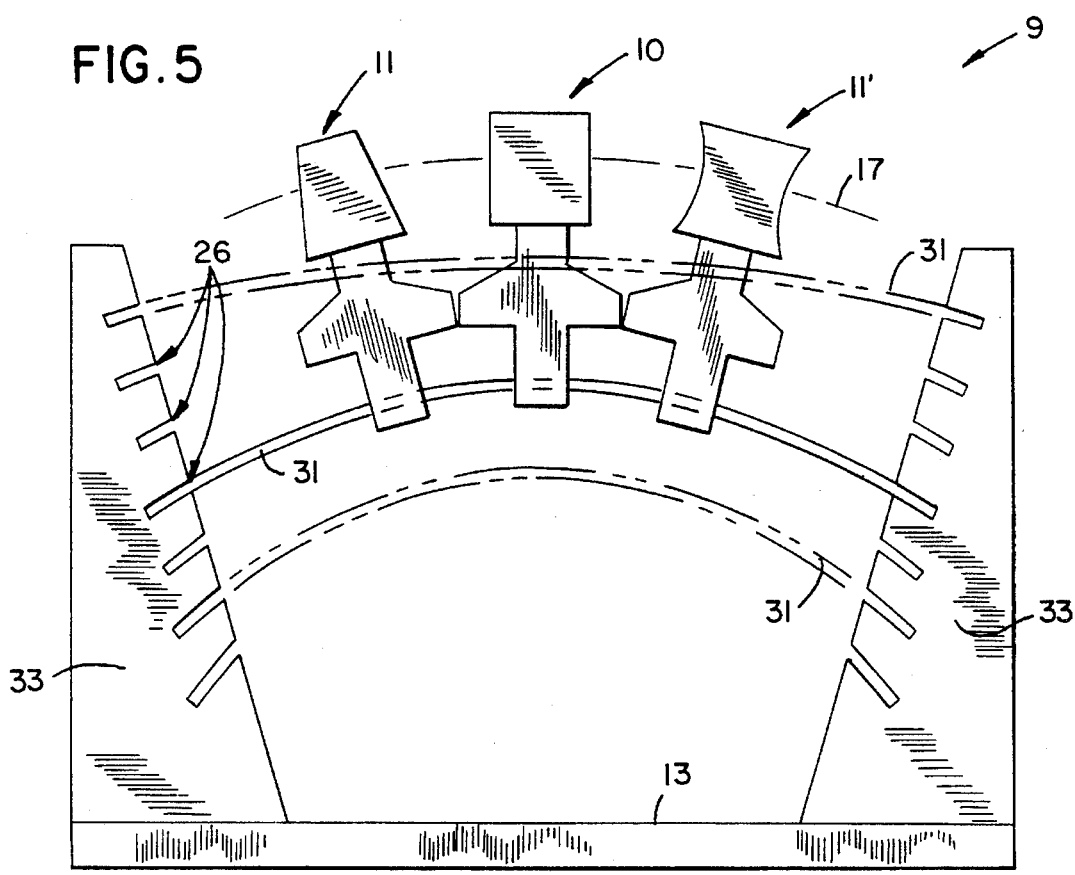
FIG. 5 shows a front elevational view of a mechanism for adjusting the radius of the curvilinear arc of the vertebral sections for downward curves.

Referring to FIG. 5, the curvature of the metal spring 31 and hence of the spinal axis 17 can be adjusted by the use of a series of transverse slots 26 cut in the inner opposed faces of wedge shaped side pieces 33 rising upward at either longitudinal end of the base 13. The transverse slots 26 receive the ends of the metal spring 31. The wedge shaped sides 33 slope inward, toward each other as one progresses downward toward the base 13 so that a slot 26, lower on each wedge shaped side 33, is closer to a slot 26 of corresponding height on the opposed wedge shaped side 33.

Thus, the use of the lower slots 26 provides a smaller radius of curvature to the metal spring 31 and spinal axis 17.

Each slot 26 is numbered (not shown) so that corresponding slots 26 equally spaced above the base 13 have the same number to guide the user into correctly inserting the metal spring 31. The numbers may indicate the radius of curvature of the spinal axis 17 so produced when those slots 26 are used. The slots 26 are slanted to conform generally with the curvature of the metal spring 31 when it is inserted into slots of the same number.

Figure 6:
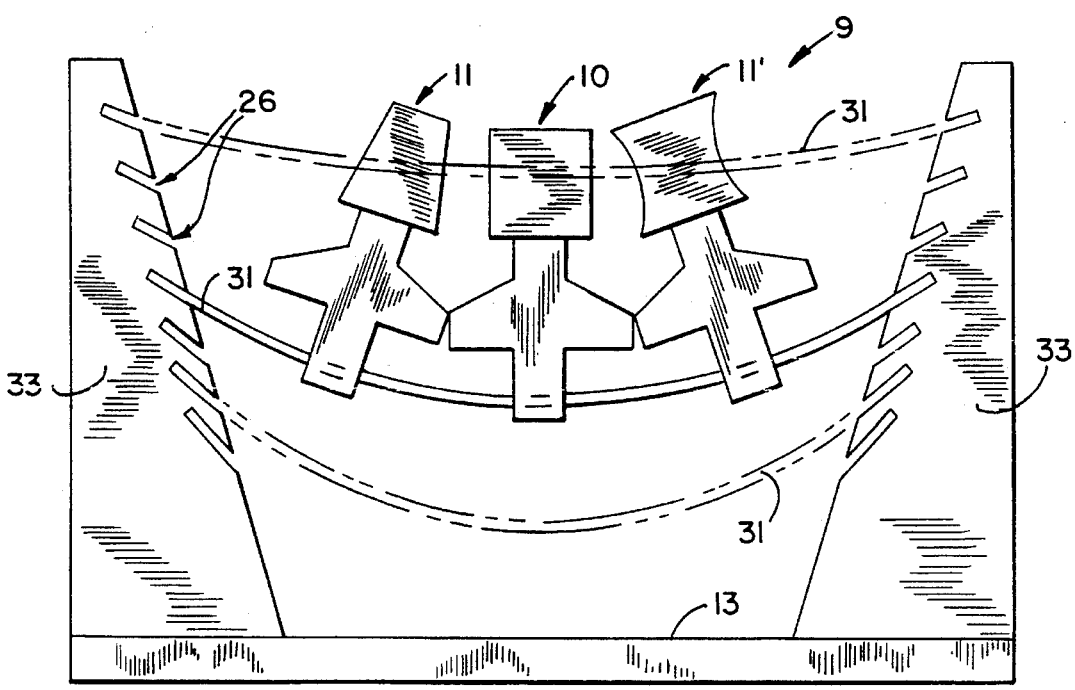
FIG. 6 is a figure similar to that of FIG. 5 showing a mechanism for adjusting the radius of the curvilinear arc of the vertebral sections for upward curves.

The curvature produced by this arrangement of FIGS. 4 and 5 is downward, the metal spring 31 forming an arch rising above the base 13. Referring to FIG. 6, changing the angle of the slots 26 permits the curvature of the meal spring 31 and the spinal axis 17 to be upward.

Like the slots 26 of FIG. 5, the slots 26 of FIG. 6 are angled along their depth to accommodate the expected angle of entry of the metal spring 31. The slots 26 are numbered starting at the lower most slot so that inserting the metal spring 31 into correspondingly numbered slots 26 provides an indicated radius of curvature.

Figure 7:
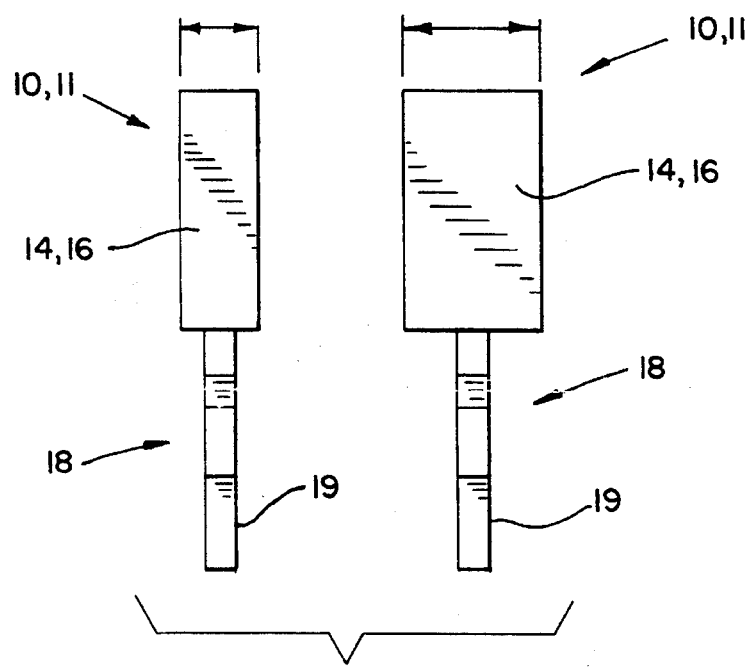
FIG. 7 shows a side elevational view of two vertebra sections illustrating that the width of the vertebral bodies can also be varied.

In the preferred embodiment of the present invention, the bone equivalent density of the vertebral bodies would be known and varied from vertebra to vertebra. Thus, the phantom of the present invention could simultaneously be used to calibrate the determination of bone density (BMD) or bone mineral content (BMC) on a bone densitometer as well as calibrate the x-ray machine to minimize distortion and verify that the morphometry software is operating properly. This is particularly true of morphometric software that combines the measurement of BMD and morphometric dimensions to produce a fracture indication. If the phantom of the present invention is made of a uniform material, the density of individual vertebra could be a function of the thickness of the material. Thus, certain vertebra of the phantom could be made thicker and thus more dense than other vertebra as illustrated in FIG. 7. The effect of the different attenuation between cortical (outer) bone of the vertebrae and trabecular (inner) bone could be simulated by constructing the inner core of the vertebral bodies 16 and 14 of a less attenuating material coated with a more attenuating material, most simply implemented by changing the amount of attenuating material mixed into a plastic binder.

The representative vertebra of all FIGS. 1–7 are formed of a radiopaque material having sufficient x-ray absorption and attenuation characteristics such that a positive image of the representative vertebrae is produced when imaged on an x-ray machine. In contrast, FIG. 8 illustrates that the representative vertebrae 10 and 11 could produce a negative image and still fall within the scope of the present invention. FIG. 8 illustrates a phantom 9 which is comprised of a block 41 of x-ray absorbing material, such as Lucite. Material is removed from the block 41 in form and manner to produce the outline of at least one vertebra 10 representative of a normal human vertebra and at least One adjacent vertebra 11 representative of a deformed human vertebra. Thus, when the block 41 is imaged by an x-ray machine, a negative image of the vertebral bodies is produced. Here, the radiation attenuation of the vertebral bodies is near zero.

Referring now to FIG. 9, in a further embodiment of the present invention, the representative vertebrae 10 and 11 are encased in a material 51 having x-ray absorbing and attenuation characteristics similar to soft tissue or water. This material could, in fact, be water. In such an embodiment, the representative vertebrae 10 and 11 would be inserted into the base 13 forming the bottom of an aquarium-like container 52 which is then filled with water. Alternatively, a material such as Lucite could be placed around the representative vertebrae 10 and 11.

Referring to FIG. 10, an entire spine may be produced according to the present invention by providing an integral spinal support 42 formed of the joining of multiple posterior elements 18 to follow a curved path of a typical spine. The vertebral bodies 14 and 16 would be removable per the description accompanying FIG. 3 so that deformed vertebral bodies may be placed at any position.

In this embodiment, the representative vertebrae include all of the thoracic and lumbar vertebrae at least one of which is representative of a vertebral deformity. For example, T7 through T9 of this embodiment represent wedge deformities and T12, L2 and L3 represent biconcavity deformations. It should be noted that the curvilinear pattern may exist in both the sagittal and coronal planes thus increasing the ability to more correctly mimic the normal or pathologic state.

Common to all the embodiments of the present invention is the requirement that the exterior dimensions of the vertebral body be known or easily determined. For that reason, it is preferred that the representative vertebrae be more cubiform than one would ordinarily desire for an anthropomorphic model.

It is understood that the invention is not confined to the particular embodiments set forth herein as illustrated, but embraces such modified forms thereof as come within the scope of the following claims.

What I claim is:

1. An x-ray phantom, comprising:
   a first vertebral model formed of a material having a first predetermined radiation attenuation and sized to substantially resemble a human vertebra;
   a second vertebral model affixed with respect to the first vertebral model and formed of a material having a second predetermined radiation attenuation and sized to substantially resemble a human vertebra with a clinically recognized vertebral deformity.

2. The x-ray phantom as recited in claim 1 wherein the first vertebral model is sized to substantially resemble a human vertebra without a clinically recognized vertebral deformity.

3. The x-ray phantom as recited in claim 1 wherein the first and second predetermined radiation attenuations are substantially equivalent to an attenuation produced by human vertebral bone.

4. The x-ray phantom as recited in claim 1 wherein the first and second vertebral models are surrounded by an attenuating material having a third predetermined radiation attenuation.

5. The x-ray phantom as recited in claim 4 wherein the attenuation of the surrounding attenuating material is substantially equivalent to an attenuation of soft tissue.

6. The x-ray phantom as recited in claim 4 wherein the first and second predetermined radiation attenuations are less than the attenuation of the surrounding attenuating material.

7. The x-ray phantom as recited in claim 1 wherein the first and second predetermined radiation attenuations are equal.

8. The x-ray phantom as recited in claim 1 wherein the second vertebral model is affixed relative to the first vertebral model to represent a section of a curved spine.

9. The x-ray phantom as recited in claim 1 including a flexible mounting rail having an adjustment mechanism for controlling the curvature of the mounting rail and where the first and second vertebral models are attached to the curved mounting rail to assume a relative position dictated by the curvature of the mounting rail.

10. An x-ray phantom as recited in claim 1, wherein one of the first and second vertebral models are constructed of a material including hydroxyapatite.

11. An x-ray phantom as recited in claim 1, wherein one of the first and second vertebral models are constructed of a material including aluminum.

12. An x-ray phantom as recited in claim 1, wherein the first and second vertebral models have an anterior height, a middle height and a posterior height and wherein at least one of the anterior height, the middle height and the posterior height differ between the first and second vertebral models.

13. An x-ray phantom as claimed in claim 2, wherein first and second predetermined radiation attenuation is different and produced by said vertebral models having different thicknesses.

14. The x-ray phantom as recited in claim 1 wherein the clinically recognized vertebral deformity is selected from the group consisting of: wedge deformities, endplate biconcavity, and endplate hypertrophy.

15. A method of employing an x-ray phantom having a first vertebral model formed of a material having a first predetermined radiation attenuation and sized to substantially resemble a human vertebra and a second vertebral model affixed with respect to the first vertebral model and formed of a material having a second predetermined radiation attenuation and sized to substantially resemble a human vertebra with a clinically recognized vertebral deformity, the method comprising the steps of:

positioning the x-ray phantom with respect to radiographic equipment;

obtaining a radiographic image of the x-ray phantom so positioned;

establishing the classification of the first and second vertebral models as having or not having clinically recognized vertebral deformity based on direct physical measurement of the dimensions of the vertebral models;

analyzing the image to classify the first and second vertebral bodies as having or not having clinically recognized vertebral deformity; and comparing the classification from the image with the classification by direct physical measurement to evaluate the analyses.

16. The method as recited in claim 15 wherein the first vertebral model substantially resembles a human vertebra without a clinically recognized vertebral deformity and wherein the comparison step evaluates both erroneous classification of the first vertebral model as having clinically recognized vertebral deformity and the second vertebral model as not having clinically recognized vertebral deformity.

17. The method as recited in claim 15 wherein the radiographic equipment also provides bone density information and including the steps of:

establishing the expected bone density values of the first and second vertebral models from their predetermined radiation attenuations;

obtaining bone density values for the first and second vertebral models by radiographic analyses; and comparing the bone density values from the predetermined radiation attenuations to the bone density values obtained to evaluate the radiographic analyses.

18. A method of employing an x-ray phantom having a first vertebral model formed of a material having a first predetermined bone density value and sized to substantially resemble a human vertebra and a second vertebral model affixed with respect to the first vertebral model and formed of a material having a second predetermined bone density value and sized to substantially resemble a human vertebra with a clinically recognized vertebral deformity, the method comprising the steps of:

establishing the classification of the first and second vertebral models as evidencing or not evidencing osteoporosis based on direct physical measurement of the dimensions of the vertebral models and their bone density values;

positioning the x-ray phantom with respect to an imaging densitometer;

obtaining a radiographic image of the x-ray phantom so positioned, the image indicating dimensions and measured bone density of the first and second vertebral models;

analyzing the image to classify the first and second vertebral bodies as evidencing or not evidencing osteoporosis based on a morphometric analyses of the radiographic image and the obtained bone density values; and comparing the classification from the image with the classification by direct physical measurement of the first and second vertebral models to evaluate the analyses of the image.

* * * * *